(12) United States Patent
Kaku et al.

(10) Patent No.: US 9,414,794 B2
(45) Date of Patent: Aug. 16, 2016

(54) MOBILE X-RAY IMAGING APPARATUS

(71) Applicant: CANON KABUSHIKI KAISHA, Tokyo (JP)

(72) Inventors: Wataru Kaku, Yokohama (JP); Naofumi Sekine, Kawasaki (JP); Nobuo Komiya, Yokohama (JP); Yoshiki Kuno, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 14/181,527

(22) Filed: Feb. 14, 2014

(65) Prior Publication Data
US 2014/0233705 A1 Aug. 21, 2014

(30) Foreign Application Priority Data
Feb. 19, 2013 (JP) .................................. 2013-030155

(51) Int. Cl.
*A61B 6/00* (2006.01)
*A61B 6/10* (2006.01)
(52) U.S. Cl.
CPC ................. *A61B 6/4405* (2013.01); *A61B 6/10* (2013.01); *A61B 6/4233* (2013.01); *A61B 6/54* (2013.01); *A61B 6/586* (2013.01)
(58) Field of Classification Search
USPC ......................................... 378/117, 197, 198
See application file for complete search history.

(56) References Cited

U.S. PATENT DOCUMENTS

| | | | | |
|---|---|---|---|---|
| 5,425,069 A | * | 6/1995 | Pellegrino et al. | 378/198 |
| 5,997,176 A | * | 12/1999 | Fairleigh | 378/196 |
| 6,126,314 A | * | 10/2000 | Morasse | G03B 42/045 378/167 |
| 2003/0198317 A1 | * | 10/2003 | Nakagawa | A61B 6/4405 378/62 |
| 2004/0066899 A1 | * | 4/2004 | Araki | A61B 6/4283 378/102 |
| 2009/0046463 A1 | * | 2/2009 | Coombs | A61B 6/4405 362/253 |
| 2011/0317816 A1 | * | 12/2011 | Bechard | A61B 6/00 378/98.8 |
| 2013/0170619 A1 | * | 7/2013 | Kamitake | A61B 6/4405 378/62 |

FOREIGN PATENT DOCUMENTS

| | | |
|---|---|---|
| JP | 2009055290 A | 3/2009 |
| JP | 2012005731 A | 1/2012 |
| JP | 2012019279 A | 1/2012 |
| JP | 2012110702 A | 6/2012 |

\* cited by examiner

*Primary Examiner* — Robert Kim
*Assistant Examiner* — David E Smith
(74) *Attorney, Agent, or Firm* — Canon USA Inc., IP Division

(57) ABSTRACT

A mobile X-ray imaging apparatus includes: a mobile cart having a casing as an exterior member; an X-ray generation unit that can be stored in the casing; a handle portion arranged on an upper portion of the casing; and a movable portion having the handle portion and configured to be alternately stored in and pulled out from the casing, wherein an upper portion of the movable portion is pulled out in an inclined state from the mobile cart through a drawing-out operation performed on the handle portion by the operator.

10 Claims, 6 Drawing Sheets

MOBILE X-RAY IMAGING APPARATUS

BACKGROUND OF THE INVENTION

1. Field of the Invention

The present invention relates to a mobile X-ray imaging apparatus.

2. Description of the Related Art

X-ray imaging is performed in a patient room or an operation room in the hospital by a mobile X-ray imaging apparatus, which is mounted on a mobile cart. When X-ray imaging is to be performed, the mobile X-ray imaging apparatus is transported from a storage place to an X-ray imaging place, and when the X-ray imaging is completed, it is conveyed to the storage place again to be stored there. Thus, there has been a demand for a mobile X-ray imaging apparatus which is easy to transport and convenient to store in reduced spaces.

Japanese Patent Application Laid-Open No. 2012-110702 discloses a mobile X-ray imaging apparatus improved in terms of calmness during conveyance and comfort for the operator owing to a driving wheel suspension system.

Japanese Patent Application Laid-Open No. 2012-5731 discloses a mobile X-ray imaging apparatus which can be stored with reduced external size owing to a mechanism for sliding an arm vertically and horizontally.

However, in the mobile X-ray imaging apparatus disclosed in Japanese Patent Application Laid-Open No. 2012-110702, the main body side surface is substantially perpendicular to the floor surface, so that while superior in storage property, this apparatus has a problem to be solved in terms of conveyance property. Further, the main body rear surface opposite the operator is substantially perpendicular to the floor surface during conveyance, so that the operator who walks holding a handle portion would be awkwardly positioned for walking.

The mobile X-ray imaging apparatus discussed in Japanese Patent Application Laid-Open No. 2012-5731 can be stored with reduced external size owing to the mechanism for sliding the arm vertically and horizontally. However, the main body side surface is substantially perpendicular to the floor surface, or the lower portion thereof is protruded and inclined, so that a side surface of the main body may pose an obstacle for the operator during transporting or operating the apparatus.

SUMMARY OF THE INVENTION

The present invention is directed to a mobile X-ray imaging apparatus with improved conveyance and storage properties.

According to an aspect of the present invention, a mobile X-ray imaging apparatus includes: a mobile cart having a casing as an exterior member; an X-ray generation unit that can be stored in the casing; a handle portion arranged on an upper portion of the casing; and a movable portion having the handle portion and configured to be stored in or pulled out from the casing, wherein an upper portion of the movable portion is pulled out in an inclined state from the mobile cart through a drawing-out operation performed on the handle portion by the operator.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1A:
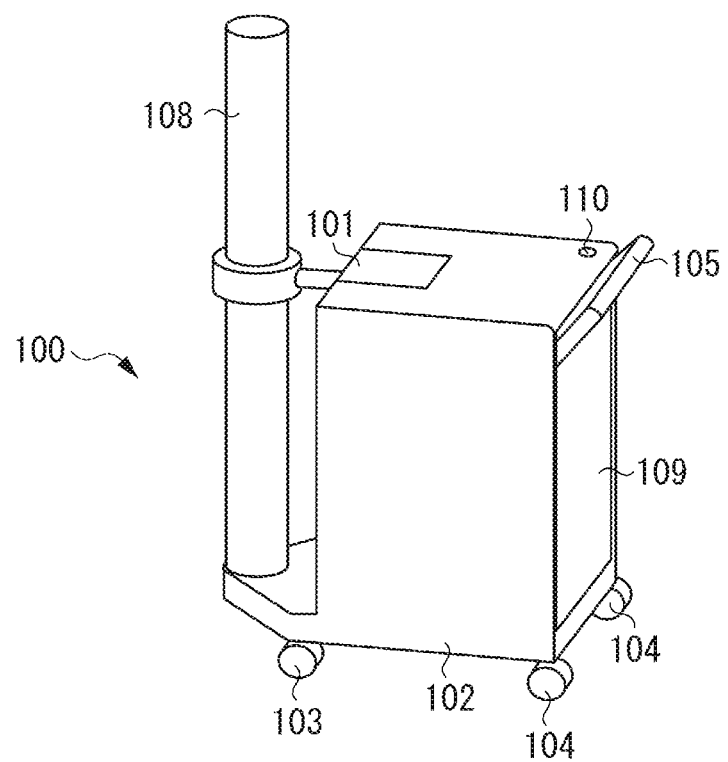
FIGS. 1A, 1B, and 1C are a left-hand rear perspective view, a left-hand side view, and a top view illustrating the outward appearance of a mobile X-ray imaging apparatus according to an exemplary embodiment of the present invention.
Figure 1B:
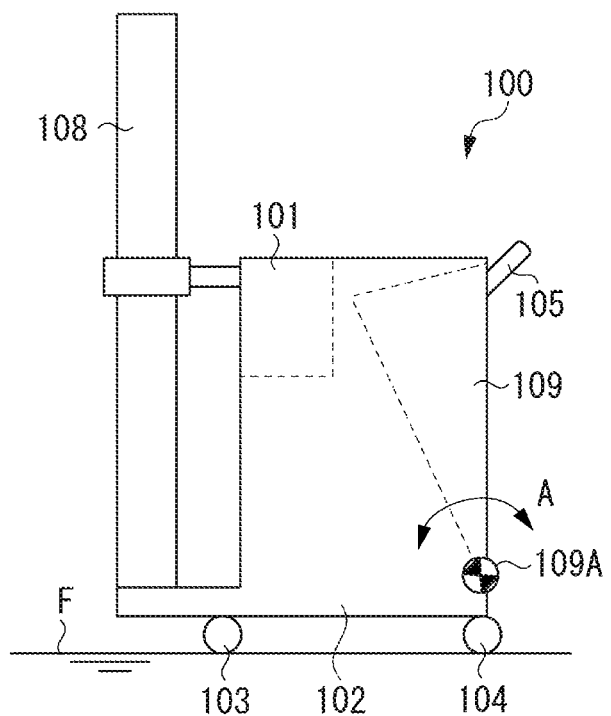
Figure 1C:
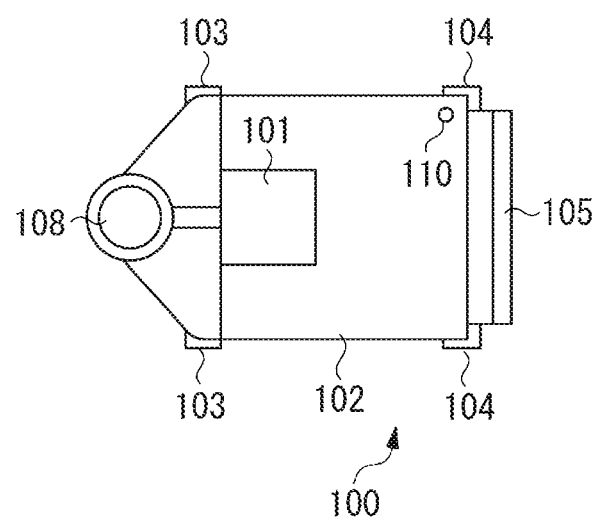

In the following, a mobile X-ray imaging apparatus according to an exemplary embodiment of the present invention will be described with reference to the drawings. In the following description, the same reference numerals are used for the same or equivalent elements. FIGS. 1A, 1B, and 1C are external views of a mobile X-ray imaging apparatus 100 according to a first exemplary embodiment of the present invention when in a stored state. FIG. 1A is a perspective view of the apparatus as seen from the left-hand rear side, FIG. 1B is a left-hand side view thereof, and FIG. 1C is a top view thereof. As illustrated in FIG. 1A, the mobile X-ray imaging apparatus 100 includes a casing 102 which has in the upper surface (upper portion) thereof a recess for accommodating an X-ray generation unit 101. The X-ray generation unit 101, which emits X-rays (e.g., for medical diagnosis of a subject), is configured to be stored in the recess formed in the upper portion of the casing 102. The X-ray generation unit 101 is, for example, an X-ray tube configured to apply thermal electrons emitted from a filament heated to a high temperature, to an X-ray target consisting of bulk metal, in order to generate X-rays on the incident side of the electron beam.

A casing 102 is an external member constituting a mobile cart, and is capable of accommodating the X-ray generation unit 101. The recess is preferably larger than the X-ray generation unit 101. More specifically, the upper surface of the casing 102 is formed so as to allow the X-ray generation unit 101 to be fitted and accommodated in it. When the X-ray generation unit 101 is accommodated in the casing 102, the X-ray generation unit 101 does not protrude from the upper surface of the casing 102. As illustrated in FIG. 1, the upper surface of the casing 102 is flush with the upper surface of the X-ray generation unit 101. In other words, the upper surface of the casing 102 with the X-ray generation unit 101 placed therein is flat. This allows an operator transporting the mobile cart to have an open view of the environment free of obstructions. In the rear portion of the casing 102, there is provided a movable portion 109 which is described below. In the accommodated (stored) state as illustrated in FIGS. 1A, 1B, and 1C, the movable portion 109 is placed within the casing 102. The back surface or rear surface of the casing 102 formed by a portion of the movable portion 109 is substantially perpendicular to the floor surface F. Further, inside the casing 102, there are provided a processing unit (not illustrated) configured to perform the requisite information communication and processing, and a drive unit or driving device (not illustrated) configured to drive and control, for example, the rotation of wheels arranged under the mobile cart.

A pair of rear wheels 104 flexibly moves and changes their directions to the right and left. By changing the orientation of the rear wheels 104, the operator can change the moving direction of the mobile X-ray imaging apparatus 100. In other words, the rear wheels 104 function as steering wheels. In the present exemplary embodiment, the front wheels 103 are a pair of stationary wheels the orientation of which is fixed (typically a back and forth direction), and which are connected to the driving device. The above-mentioned processing unit controls the driving device, whereby the front wheels 103 function as driving wheels, enabling the mobile X-ray imaging apparatus 100 to move forwards and backwards.

A handle portion 105 is connected with the movable portion 109. The handle portion 105 is a member configured to be grasped by the operator when the mobile X-ray imaging apparatus 100 is moved or when the movable portion 109 is drawn out rearwards. The handle portion 105 is fixed so as to protrude above the rear surface of the casing 102.

A display unit 106 (see FIG. 2A) is a unit for displaying information related to X-ray imaging, a setting screen, etc. A liquid crystal display (LCD) or the like is used as the display unit. An operation unit 107 is operated by the operator when switching the setting or a display related to X-ray imaging. The operation unit 107 is formed by cross keys, push switches, etc. It is also possible for the display unit 106 and the operation unit 107 to be integrally formed as a touch screen in which a transparent input unit, etc. are arranged on the front surface of the display, that is, the operator-side surface. A column 108 is a columnar member for fixing the X-ray generation unit 101 at various positions, and is disposed in a forward position (front) of the mobile cart. The column 108 is connected with the driving device inside the casing 102, and can change the position of the X-ray generation unit 101 through electrical control.

The movable portion 109 can be alternately drawn out rearwards and accommodated in the interior of the casing according to the condition of use of the mobile X-ray imaging apparatus 100. As illustrated in FIG. 1B, in the present exemplary embodiment, the movable portion 109 is formed, for example, in the shape of a triangular prism arranged upside down. That is, the movable portion 109 is supported at the triangle-corner (apex of the prism) which situated at the rear lower end of the casing 102. Specifically, the movable portion 109 is pivotably, at the lower portion of the rear surface of the casing 102, so as to be rotatable around a pivot 109A (as indicated by the arrow A in FIG. 1B). In the accommodated or stored state illustrated in FIGS. 1A and 1B, the movable portion 109 is accommodated within the casing 102, and the back surface of the mobile X-ray imaging apparatus 100 is substantially perpendicular to the floor surface F, so that it is possible to compactly store the movable portion 109 without increasing an area of the apparatus occupying the floor surface F in plan view.

A key insertion portion 110 is a keyhole into which the operator inserts a key and turns it to enable use of the mobile X-ray imaging apparatus 100. According to the rotational angle of the key, it is possible to design the apparatus so as to allow control of various lock and release functions, such as the lock and release of the wheels (the front wheels 103 and the rear wheels 104), and of X-ray application, as well as the a pulled-out state of the movable portion 109.

Figure 2A:
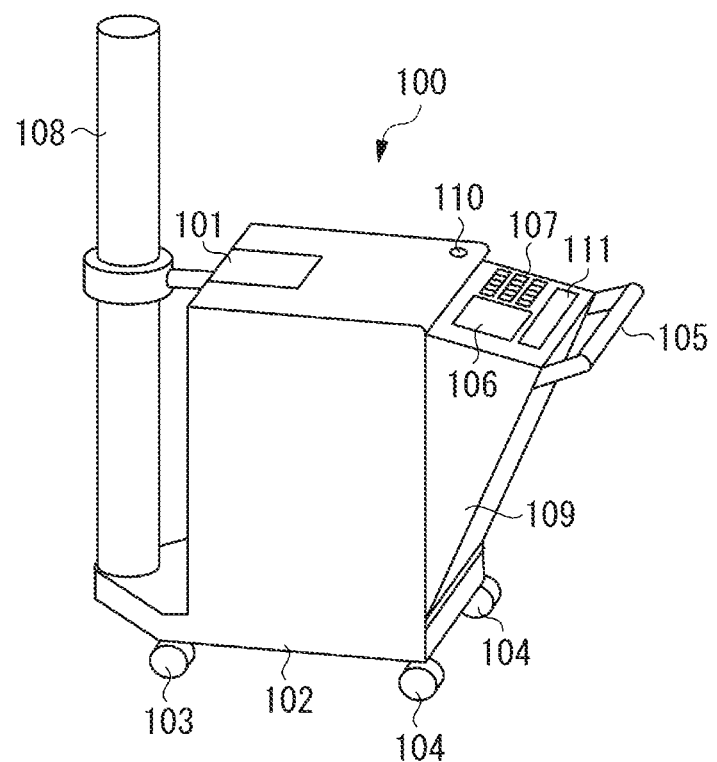
FIGS. 2A, 2B, and 2C are a left-hand rear perspective view, a left-hand side view, and a top view illustrating the outward appearance of the mobile X-ray imaging apparatus according to the exemplary embodiment of the present invention at the time of pulling-out.

Further, referring to FIG. 2A, etc., an X-ray detection sensor storage portion 111 is a portion into which an X-ray detection sensor (e.g., a flat panel detector (FPD) not illustrated) is inserted, so that the X-ray detection sensor can be carried along with the mobile X-ray imaging apparatus 100.

Figure 2B:
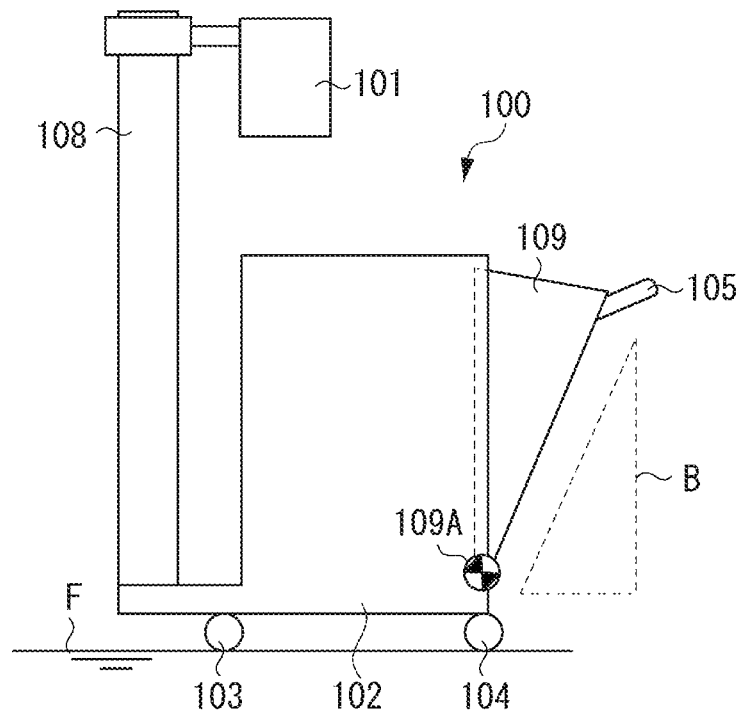
Figure 2C:
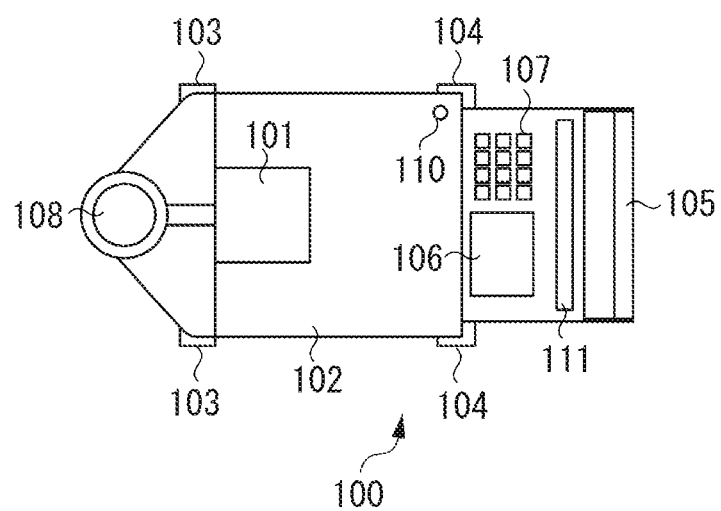

FIGS. 2A, 2B, and 2C are external views illustrating the mobile X-ray imaging apparatus 100 according to the present exemplary embodiment at the time of pulling out, or otherwise referred to as an operating state. FIG. 2A is a perspective view of the apparatus as seen from the left-hand rear side, FIG. 2B is a left-hand side view thereof, and FIG. 2C is a top view thereof.

When, in the stored state as illustrated in FIGS. 1A, 1B, and 1C, the operator performs operation on the apparatus to draw the handle portion 105 rearwards, the movable portion 109 rotates (swivels or pivots) around the pivot 109A, and the apparatus is in a pulled-out or operative state as illustrated in FIGS. 2A, 2B, and 2C is attained. As illustrated in FIG. 2B, in the pulled-out state, the upper portion of the movable portion 109 is drawn out in an inclined state with respect to the casing 102, and it protrudes from the casing 102, so that a space B is generated under the movable portion 109. Advantageously, when the operator is walking while holding the handle portion 105 to transport the mobile X-ray imaging apparatus 100, the lower extremities (in particular the feet) of the operator are located in this space B. Accordingly, it is possible to prevent the operator's legs or feet from hitting the mobile X-ray imaging apparatus 100. Further, since the space B is formed, the operator can walk smoothly and in an appropriate manner, making it possible to guarantee a high level of safety from the viewpoint of handling the mobile X-ray imaging apparatus 100.

As described above, according to the present invention, the mobile X-ray imaging apparatus has the mobile cart equipped with the casing 102, the X-ray generation unit 101 configured to generate X-rays, the handle portion 105 arranged on top of the casing 102, and the movable portion 109 configured to be alternated accommodated in and pulled out from the casing 102 by the handle portion 105. Advantageously, when the movable portion 109 is pulled out, both the upper and rear surfaces of the movable portion 109 are in an inclined state with respect to the mobile cart through the operation of the handle portion 105 by the operator. When the upper surface of the movable portion 109 is inclined with respect to the mobile cart, as shown in FIGS. 2A and 2B, the screen 106 and operating unit 107 are more conveniently positioned for the operator's access. When the movable portion 109 is in the stored state, the back surface of the mobile X-ray imaging apparatus 100 is substantially perpendicular to the floor surface F. As a result, the mobile X-ray imaging apparatus 100 can be very adequately stored. On the other hand, when the movable portion 109 is in the pulled-out state, the back surface of the main body of the apparatus is backwardly inclined such that the upper portion thereof protrudes, so that it is possible to provide a mobile X-ray imaging apparatus 100 of satisfactory conveyance property.

In the mobile X-ray imaging apparatus 100 configured to change its moving direction by means of the rear wheels 104, when steering the mobile cart to the right or left, the leg of the operator moving forwards can coincide with the steering direction, so that there is a strong possibility that his leg may hit the apparatus. In the present invention, in contrast, there is sufficient leeway in terms of space due to the space B, making it possible to eliminate danger of such an accident. More specifically, according to the present invention, in the stored state, the movable portion is compactly accommodated within the casing, thus providing a very satisfactory storage property. On the other hand, in the pulled-out state, the movable portion is inclined backwards, so that it is possible to realize a mobile X-ray imaging apparatus of a satisfactory conveyance property.

Generally speaking, there is especially danger of such an accident as mentioned above in, for example, a power drive type mobile X-ray imaging apparatus 100 configured to drive its wheels with power. However, the present invention is not only applicable to the power drive type mobile X-ray imaging apparatus, but also to a non-power-drive type mobile X-ray imaging apparatus equipped with no drive unit.

Next, a mobile X-ray imaging apparatus according to a second exemplary embodiment of the present invention will be described. In the second exemplary embodiment, there is provided an operation unit, wherein the operation unit is accommodated so as not to allow operation when the movable portion 109 has not been drawn out. The present exemplary embodiment will be described in detail as follows. As illustrated in FIGS. 2A, 2B, and 2C, the mobile X-ray imaging apparatus 100 according to the second exemplary embodiment of the present invention has the operation unit 107 on the upper surface of the movable portion 109. When the X-ray generation unit 101 is in the storage state, there is no possibility that the operator operates the operation unit 101, so that it is highly probable that any operation performed on the operation unit 107 when in the storage state is an erroneous operation.

When the mobile X-ray imaging apparatus 100 is in the storage state as illustrated in FIGS. 1A, 1B, and 1C, the operation unit 107 is accommodated within the casing 102, so that it does not accept any operation performed by the operator, thus making it possible to prevent erroneous operation. In the pulled-out state illustrated in FIGS. 2A, 2B, and 2C, the operation unit 107 is exposed away from the casing 102 together with the movable portion 109, so that it can accept the operation performed by the operator.

In this way, in the mobile X-ray imaging apparatus 100 according to the second exemplary embodiment of the present invention, it is possible to prevent erroneous operation of the apparatus when it is in the storage state, and, when it is in the pulled-out state, it can accept an input operation performed thereon.

In addition to the operation unit 107, the mobile X-ray imaging apparatus 100 according to the present invention includes, on the upper surface of the movable portion 109, a display unit 106 and an X-ray detection sensor storage portion 111 (See FIG. 2A, etc.). Such portions or members can be accommodated within the casing 102 when the movable portion 109 has not been drawn out.

For example, by providing the display unit 106 on the upper surface of the movable portion 109, it is possible to prevent damage from the outside of the display unit 106 in the storage state. In addition to this, in the pulled-out state, it is possible to visually recognize the display unit 106. As a result, when carrying the mobile X-ray imaging apparatus 100, the operator can check information on the subject and its inspection by means of the display unit 106. Further, by providing the X-ray detection sensor 111, for example, on the upper surface of the movable portion 109, it is possible, in the storage state, to prevent the X-ray detection sensor 111 from being lost by theft, and, at the time of pulling out, it is possible to extract the X-ray detection sensor 111.

Further, a mobile X-ray imaging apparatus according to a third exemplary embodiment of the present invention will be described. In the third exemplary embodiment, the application of X-rays is controlled according to the condition of the movable portion 109. The present exemplary embodiment will be described specifically as follows.

Figure 3:
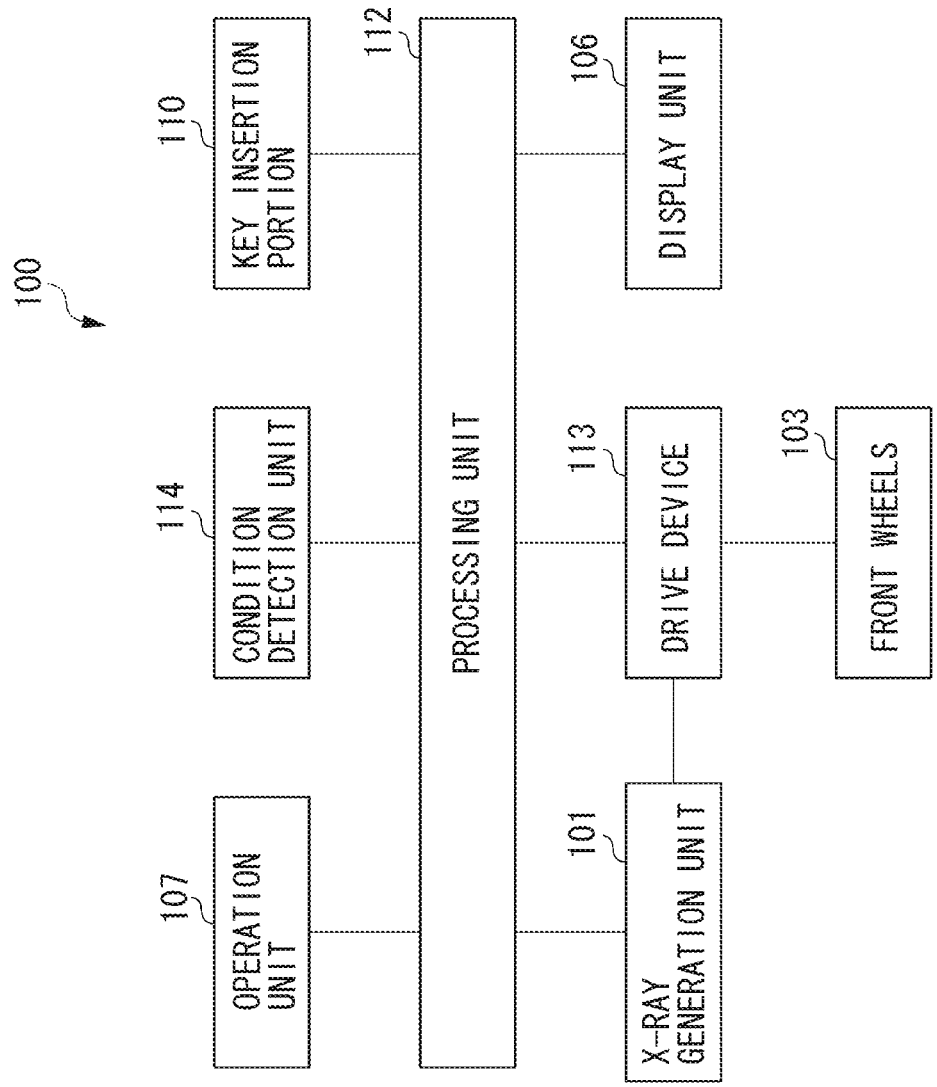
FIG. 3 is a functional block diagram illustrating a construction example of the mobile X-ray imaging apparatus according to the exemplary embodiment of the present invention.

FIG. 3 is a block diagram illustrating the mobile X-ray imaging apparatus according to the present exemplary embodiment of the present invention. An X-ray generation unit 101 generates X-rays under control of a processing unit 112. Under control of the processing unit 112, the driving device 113 changes a position of the X-ray generation unit 101 with respect to the column 108, and rotates the front wheels 103. Under control of the processing unit 112, the display unit 106 displays an operation screen, imaging information, etc. The operation unit 107 transmits a command input by the operator to the processing unit 112 as an electric signal.

In the present exemplary embodiment, a condition detection unit 114 is a unit configured to detect whether the movable portion 109 of the mobile X-ray imaging apparatus 100 is accommodated within the casing 102 or has been drawn out of the casing 102, and to transmit the detection result to the processing unit 112. As to the condition detection unit 114, an opening/closing detection sensor or the like combining a magnet and a Hall integrated circuit (IC) is applicable as a so-called Hall element discussed in Japanese Patent Application Laid-Open No. 2009-55290 or Japanese Patent Application Laid-Open No. 2012-19279. For example, this Hall element can be attached to the pivot 109A of the movable portion 109, and the rotational angle thereof is tracked to detect the opening/closing condition of the movable portion 109. The processing unit 112 controls the application of X-rays, the transmission and reception of data, image processing, various image processing operations such as display control, and data storage, in order to control the operation of the mobile X-ray imaging apparatus 100. The key insertion portion 110 detects the rotational position of the key, and transmits the detection result to the processing unit 112.

Figure 4:
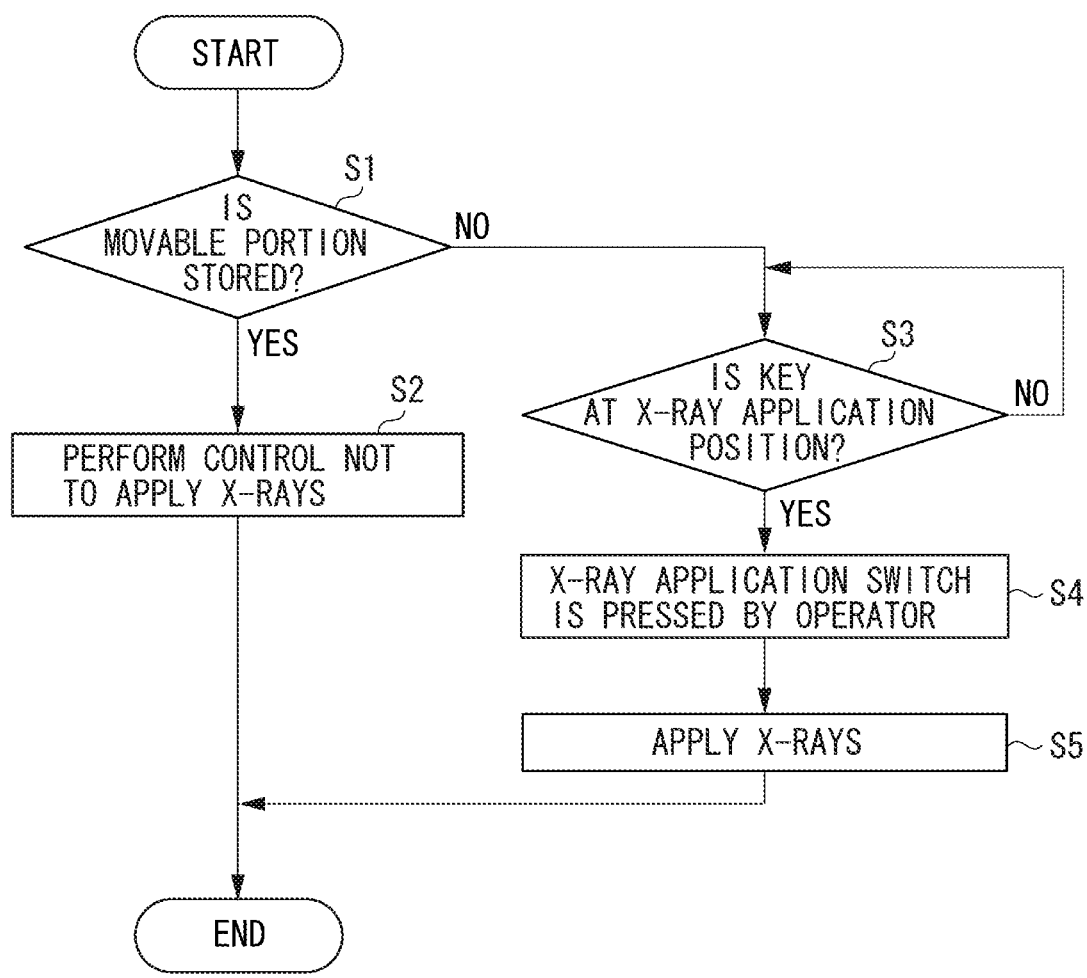
FIG. 4 is a flowchart illustrating a determination processing flow for controlling the X-ray apparatus in the mobile X-ray imaging apparatus according to the exemplary embodiment of the present invention.

FIG. 4 is a flowchart indicating the determination processing flow for the control of X-ray application based on the condition of the movable portion 109 of the mobile X-ray imaging apparatus 100 according to the present exemplary embodiment of the present invention. First, in step S1, the condition detection unit 114 detects the condition of the movable portion 109. When it is detected that the movable portion 109 is retracted, the processing unit 112 performs control, in step S2, such that the X-ray generation unit 101 emits no X-ray. This control is realized, for example, by cutting off power supply to the X-ray generation unit 101, or by putting the X-ray generation unit 101 within the casing 102 under control of the driving device 113, or by performing control such that input by the X-ray application switch of the operation unit 107 is not accepted.

On the other hand, when, in step S1, it is detected that the movable portion 109 has been drawn out, in step S3, the rotational position of the key in the key insertion portion 110 is determined. When, in step S3, it is determined that the key is at the position allowing X-ray application, the procedure advances to step S4. In step S4, when pressing of the X-ray application switch in the operation unit 107 by the operator is detected, the processing unit 112, in step S5, controls the X-ray generation unit to apply X-rays.

As described above, in the mobile X-ray imaging apparatus 100 according to the third exemplary embodiment of the present invention, it is possible to prevent an accident such as erroneous X-ray application when the movable portion 109 is stored in the casing 102.

In addition to the above-described, the present invention can assume various embodiment forms such as a system, apparatus, method, program, or storage medium. More specifically the present invention is applicable to a system composed of a plurality of apparatuses, or to a system consisting of a single apparatus.

Further, the object of the present invention can also be achieved by executing the following processing: A storage medium storing the program code of software for realizing the functions of the above-described exemplary embodiments may be supplied to a system or an apparatus. Then, the computer (or the central processing unit (CPU) or the microprocessing unit (MPU)) in the system or the apparatus reads the program code stored in the storage medium. In this case, the program code itself read out from the storage medium realizes the functions of the above-described exemplary embodiments, and the program code and the storage medium storing the program code constitute the present invention.

The desirable specific exemplary embodiments of the present invention described in detail above should not be limited to these exemplary embodiments. The present invention may also include various other embodiments without departing from the scope of the gist of the present invention. Partial combination of the above-described exemplary embodiments is also possible.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-030155 filed Feb. 19, 2013, which is hereby incorporated by reference herein in its entirety.

What is claimed is:

1. A mobile X-ray imaging apparatus comprising:
   a mobile cart having a casing;
   an X-ray generation unit configured to generate X-rays;
   a movable portion configured to be alternately stored in and pulled out from the casing by a handle portion, wherein an upper portion of the movable portion is pulled out in an inclined state from the casing; and
   an operation unit configured to operate the mobile X-ray imaging apparatus, wherein the operation unit is provided on the upper portion of the movable portion,
   wherein the operation unit is exposed when the movable portion is pulled out from the casing, and the operation unit is stored in the casing to prevent an operator from operating the operation unit when the movable portion is stored in the casing.

2. The mobile X-ray imaging apparatus according to claim 1, wherein the operation unit is exposed away from the casing as the movable portion is pulled out.

3. The mobile X-ray imaging apparatus according to claim 1, further comprising: a condition detection unit configured to detect whether the movable portion is stored in the casing or pulled out, wherein, when the detection unit has detected that the movable portion is stored in the casing, control is performed such that the X-ray generation unit emits no X-ray.

4. The mobile X-ray imaging apparatus according to claim 1, wherein the mobile cart is provided with a flexibly moving rear wheel.

5. The mobile X-ray imaging apparatus according to claim 1, wherein the mobile cart is provided with a front wheel which is a driving wheel configured to be driven by a driving device.

6. The mobile X-ray imaging apparatus according to claim 1, wherein a recess for storing the X-ray generation unit is provided in the upper portion of the casing, and wherein, when the X-ray generation unit is stored in the casing, the X-ray generation unit does not protrude from the upper surface of the casing.

7. The mobile X-ray imaging apparatus according to claim 1, wherein an X-ray detection sensor storage portion for storing an X-ray detection sensor is provided in the upper portion of the movable portion.

8. The mobile X-ray imaging apparatus according to claim 1, further comprising, a display unit configured to display a setting screen and information related to X-ray imaging provided on the upper portion of the movable portion.

9. A mobile X-ray imaging apparatus comprising:
   a mobile cart having a casing;
   an X-ray generation unit attached to a columnar member and configured to generate X-rays;
   a movable portion configured to be alternately stored in and pulled out from the casing by a handle portion attached to the movable portion; and
   an operation unit configured to operate the mobile X-ray imaging apparatus, wherein the operation unit is provided on the upper portion of the movable portion,
   wherein the operation unit is exposed when the movable portion is pulled out from the casing, and the operation unit is stored in the casing to prevent an operator from operating the operation unit when the movable portion is stored in the casing, and
   wherein, when the handle portion is pulled by an operator in a direction away from the casing, the movable portion swivels and is pulled out to an inclined state with respect to the mobile cart.

10. The mobile X-ray imaging apparatus according to claim 9, wherein the movable portion is shaped as a rectangular prism arranged with its apex in a rear lower portion of the casing, and
   wherein the movable portion is pivotably attached at the rear lower portion of the casing, so as to be rotatable around a pivot.

* * * * *